(12) United States Patent
Gnakou

(10) Patent No.: US 11,461,864 B2
(45) Date of Patent: Oct. 4, 2022

(54) FOOD ALLERGY AND FOOD AVERSION MANAGEMENT SYSTEM

(71) Applicant: Paul Kpatcha Gnakou, Randolph, MA (US)

(72) Inventor: Paul Kpatcha Gnakou, Randolph, MA (US)

( * ) Notice: Subject to any disclaimer, the term of this patent is extended or adjusted under 35 U.S.C. 154(b) by 309 days.

(21) Appl. No.: 16/743,163

(22) Filed: Jan. 15, 2020

(65) Prior Publication Data

US 2020/0250783 A1 Aug. 6, 2020

Related U.S. Application Data

(60) Provisional application No. 62/800,083, filed on Feb. 1, 2019.

(51) Int. Cl.
| | |
|---|---|
| *G06Q 50/26* | (2012.01) |
| *G16H 10/60* | (2018.01) |
| *G06Q 50/12* | (2012.01) |
| *G06Q 30/06* | (2012.01) |
| *G06K 19/06* | (2006.01) |
| *G08B 5/22* | (2006.01) |
| *G06K 7/14* | (2006.01) |
| *G06F 3/04817* | (2022.01) |
| *G06F 3/0482* | (2013.01) |

(52) U.S. Cl.
CPC ......... *G06Q 50/265* (2013.01); *G06F 3/0482* (2013.01); *G06F 3/04817* (2013.01); *G06K 7/1413* (2013.01); *G06K 7/1417* (2013.01); *G06K 19/06018* (2013.01); *G06K 19/06037* (2013.01); *G06Q 30/0633* (2013.01); *G06Q 50/12* (2013.01); *G08B 5/22* (2013.01); *G16H 10/60* (2018.01)

(58) Field of Classification Search
CPC .. G06Q 50/265; G06Q 30/0633; G06Q 50/12; G06F 3/04817; G06F 3/0482; G08B 7/068; G16H 20/60
See application file for complete search history.

(56) References Cited

U.S. PATENT DOCUMENTS

| | | | | |
|---|---|---|---|---|
| 2012/0009550 A1* | 1/2012 | Gayle | ............... | G09B 19/0092 434/127 |
| 2012/0253828 A1* | 10/2012 | Bellacicco, Jr. | ... | G06Q 30/0201 705/1.1 |
| 2013/0085345 A1* | 4/2013 | Geisner | ............... | G02B 27/017 600/300 |
| 2013/0211814 A1* | 8/2013 | Derks | ................... | G06Q 50/12 704/2 |
| 2013/0290852 A1* | 10/2013 | Silverman | ............ | G06Q 50/00 715/733 |

(Continued)

*Primary Examiner* — Cao H Nguyen
(74) *Attorney, Agent, or Firm* — Lambert Shorten & Connaughton; David J. Connaughton, Jr.; Justin P. Tinger

(57) ABSTRACT

A means for food allergy management system, a smart AI driven restaurant menus on QR Code or barcode for enhanced dining experience is disclosed. This software invention brings Artificial Intelligence to restaurant menus, making them smarter, intelligent, enhanced and multilingual with advanced dish and item visuals and descriptions, strong analytics and hyperlinks to the meaning of industry terms. By bringing exceptional skills for content intelligence and ingredient safety management to menus, this invention fills the void on previously restaurant menus.

6 Claims, 3 Drawing Sheets

(56) References Cited

U.S. PATENT DOCUMENTS

| | | | |
|---|---|---|---|
| 2014/0142979 A1* | 5/2014 | Mitsunaga | G16H 10/60 705/3 |
| 2015/0073925 A1* | 3/2015 | Renfroe | G06Q 50/12 705/15 |
| 2018/0165742 A1* | 6/2018 | Singh | G06Q 30/0631 |
| 2019/0311445 A1* | 10/2019 | Werner | G06F 16/287 |

* cited by examiner

FOOD ALLERGY AND FOOD AVERSION MANAGEMENT SYSTEM

BACKGROUND OF THE INVENTION

Problem Solved

Traditional restaurant menus lag behind in the digital age, they lack in interactive intelligence, in analytical reporting skills and in multilingual translations; they are often times inscrutable due to poor or limited content description and illustrations, thus making them a burden to the entire restaurant ecosystem: for restaurant guests with food aversion and/or language barriers, dining out from traditional menus is a totally unsafe gamble; for restaurant operators, managing or updating content on traditional menus is not only expensive but time consuming and tracking how well a traditional menu and its items perform both with guests and on the revenue scale is not an easy task; in other words, traditional menus can prove dysfunctional and counterproductive in restaurant operations.

Traditional restaurant menus lack interactive intelligence, menu item visuals and descriptions; they have limited or no analytical skills and have language barriers, this makes them a burden. On traditional menus, a user with allergen concerns would have to seek more information, advice or recommendation about dishes and other menu items. The burden is even greater if the user has language barriers; for users with food allergies, the risk of anaphylactic shocks and death on traditional menus is highest.

This software invention brings intelligence and advanced capabilities to traditional restaurant menus, it also allows multiple language translations, enhanced visual descriptions and hyperlinks to the meaning of industry terms and jargons for a more informed and confident dining experience. Additionally, by adding advanced skills and interactive content intelligence to traditional menus, this invention fills both the transactional and the operational voids on previous restaurant menus.

SUMMARY OF THE INVENTION

The present disclosure concerns a food allergy management system. This system operates to automatically identify ingredients on a menu which match a user's listed allergies (including sensitivities and/or ingredients to avoid). In the prior art, a user would have to manually research what ingredients are contained in a menu item. Even in instances when a menu item is listed on a computer, the user must still navigate away from the computer menu in a web browser to manually search. This causes inefficiencies in the way a computer displayed menu operates. Moreover, in many cases, a listed ingredient may actually comprise a combination of other ingredients (soy sauce typically contains gluten, for example). This requires further searching and research outside of the visual presentation of a food menu on a display of a computer. In having to navigate away from the menu, a user is distracted, and has to carry out multiple cumbersome steps within a computer interface. The present invention solves this by, among other things, automatically generating composite information in the form of an alert presented on a display/user interface of the computer, in the same user interface which displays the menu. The system may also be programmed to automatically identify common composite ingredient in the event that the composite ingredients may itself contain an allergen.

In one aspect, the food allergy management system solves this computer-specific problem by using a first computer in networked communication with a server. The first user computer is programmed comprising a list, stored in a memory as a data file, of user allergies. This list may be input by a particular user. The server comprises a menu, and a list of ingredients for each menu item, the list comprising at least known allergens, and preferably all ingredients. The menu and the list of ingredients are stored in a memory of the server as one or more data files. The first user computer is operable to access the menu and the list of ingredients through the networked connection with the server. The menu is displayed on the user interface of the first user computer, allowing the user to scan the menu. The user computer is further operable to automatically generate customized alerts if at least one of the list of ingredients matches one of the list of user allergies, and to present an alert on a display of the first user computer. This alert may be presented as a pop up window presented over a user interface of the food allergy management system, an icon presented in-line of a user interface of the food allergy management system adjacent to a display of a menu item, or the like.

DETAILED DESCRIPTION OF THE INVENTION

Figure 1:
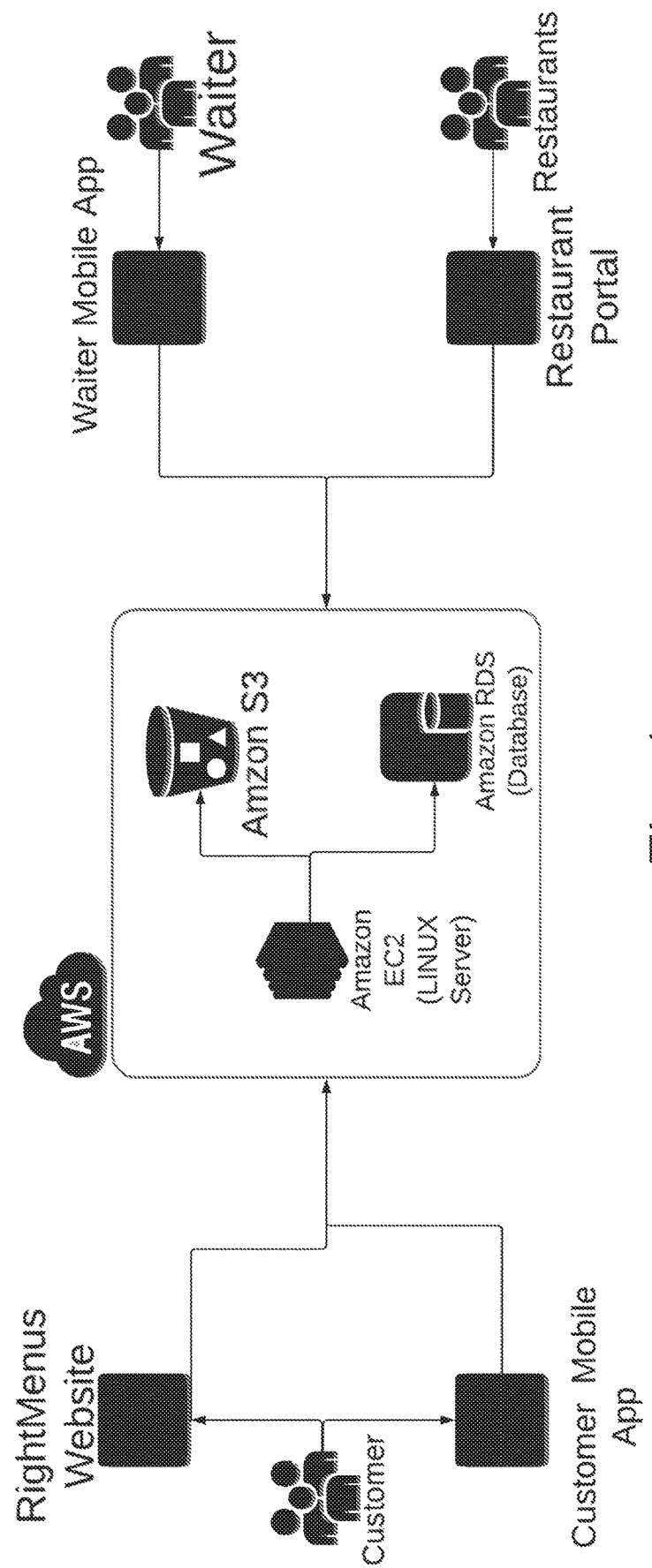
FIG. 1 provides a schematic view of an embodiment of the present food allergy management system.

As stated above, traditional restaurant menus are often times inscrutable to many users due to language barriers, lack of information, lack of skills and intelligence; this can turn the ordering process into a burden especially for users with food allergy concerns. Also, when it comes to content management and performance analytics, traditional static menus can be confusing, expensive and time consuming for restaurants; in other words, traditional menus are often dysfunctional and counterproductive for restaurants and for their guests. The invention claimed here solves this problem.

This invention brings intelligence to restaurant menus. It comes with a platform where restaurants can create smart AI driven menus that are multilingual and multifunctional with enhanced visuals and strong reporting skills. It allows users to access these AI driven menus simply by scanning a QR code or a barcode from our mobile app. The new and artificially intelligent menu on user's handset is specifically profiled to users' dining preferences and allows them to dine out with confidence: it triggers automatic alerts for food allergen and food ingredients to prevent food allergies, food intolerances and other food aversions based on a user's predefined dining profile. Even more, this invention also makes provision for audio/visual menu items description and shows specific item reviews, ratings and comments from previous diners directly on the menu so users can make a more informed choice. It also allows users to see and request the waitstaff from a button on the App where applicable by allowing the menu and the the user's application to communicate directly with the Waitstaff Mobile Application. This invention is an all-in-one solution that enables diners to manage all aspects of the dining process directly from its intelligent menus. This invention allows users to pre-order or save upcoming orders directly from the menu and be issued a reference number that is reflected in the restaurant's portal. When the user is ready to place the order, user will simply submit the saved order or communicate the reference number to the restaurant; the restaurant will locate and submit the order from the portal.

This invention is also imbedded with advanced analytical intelligence to report all aspects of the menu's interaction with users back to restaurant operators in distinct charts; it can also track each individual item's interaction with the restaurant's audience to not only report but interpret data and make informed performance suggestions with unprecedented accuracy.

The claimed invention differs from what currently exists. Previously, restaurant menus were mere lists of dishes and items with no intelligence, insufficient details and poor illustrations. This software invention brings artificial intelligence, language translation, enhanced illustrations, skills and convenience to restaurant menus, making them more productive for users and for restaurants.

This invention is an improvement on what currently exists. Current restaurant menus lack in interactive intelligence for food ingredient management, they are limited in dish and item descriptions and unsafe for diners with food aversions. By bringing artificial intelligence, thinking capability, advanced enhancements, instant language translation and industry jargon definitions to restaurant menus, this software invention fills the void on previous restaurant menus and makes them more productive.

The Version of the Invention Discussed Here Includes:
1. Computer
2. Computer Keyboard
3. Mouse or other manually manipulatable interface for controlling on-screen cursor activity
4. Handset—Mobile phone or Mobile tablet
5. Website
6. Restaurant Portal
7. Administrative Portal
8. Mobil application for waitstaff—Waitstaff App.
9. Mobile application for restaurant guests—Guest App
10. Hosting Servers
11. Dedicated QR Code or barcode Relationship Between the Components:

Computer (1) and all peripherals (2) and (3) are connected to Internet; then Website (5), Restaurant Portal (6), Mobile Application for waitstaff—Waitstaff App (8), Mobile Application for restaurant guests—Guest App (9), Handset—Mobile phone or Tablets (4), Dedicated QR Code or Barcode (11) and Administrative Portal (7) are all connected through Hosting Servers (10) were data is managed.

How the Invention Works:

FIG. 1 shows the hosting environment of RightMenus platform. The backend functionalities of this platform are performed in a cloud environment that unites the activities of Restaurants, Guests and Staff using:
  a web application (Website)
  a Restaurant Guests Mobile Application
  a Waitstaff Mobile Apps) and
  a Restaurant Portal.

Figure 2:
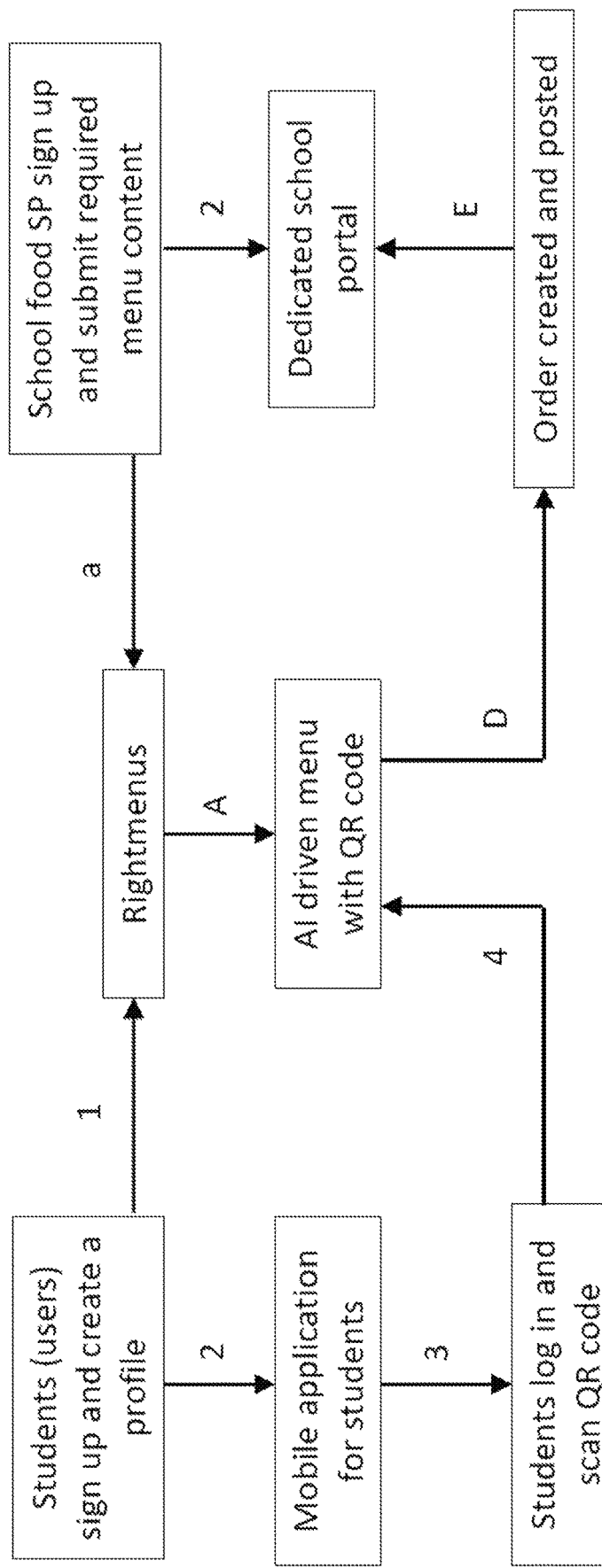
FIG. 2 provides a flow chart of one embodiment of the food allergy management system.

FIG. 2 shows a flowchart of RightMenus for schools.
  a. School Restaurant or Food S.P signs up to RightMenus and submits the menu content
  b. Restaurant or Food S.P is granted access to a dedicated Portal for enhanced content management
    A. RightMenus generates a smart AI driven menu and assigns it a QR Code.
    B. RightMenus links the smart AI driven menu to the Portal
    C. RightMenus links the smart AI driven menu to Student Mobile Application
    D. RightMenus creates the orders placed by students
    E. RightMenus submits the orders to the Portal
    1. Students Sign Up to RightMenus and create their profiles with dining preferences
    2. Students Download a mobile Application that receives content from RightMenus (C)
    3. Students login to the mobile Application to search for a school menu or scan a menu QR code to place or manage orders
    4. The order is sent to the corresponding AI driven menu service on RightMenus.

Figure 3:
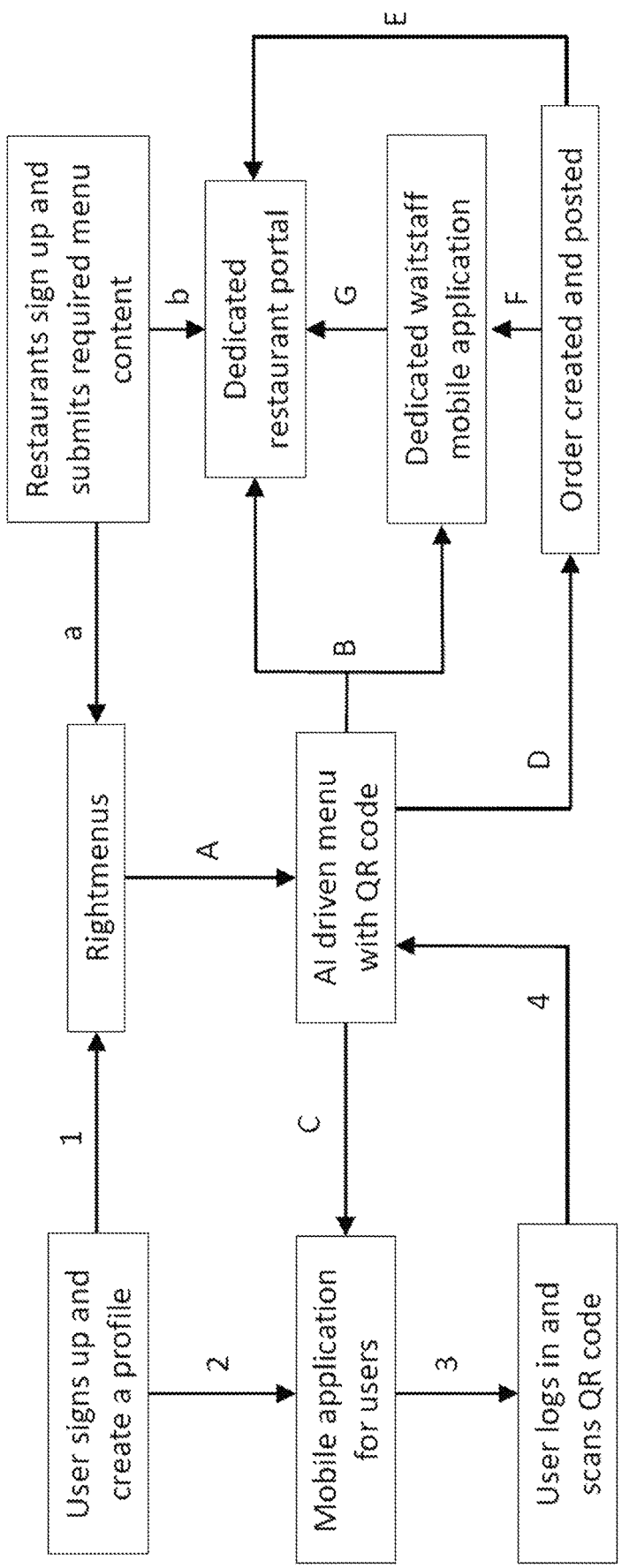
FIG. 3 provides a flow chart of another embodiment of the food allergy management system.

FIG. 3 shows a flowchart of RightMenus for restaurants.
  a. Restaurant Signs up to RightMenus and submit the menu content
  b. Restaurant is granted access to a dedicated Portal for enhanced content management.
  c. Restaurant is granted access to a dedicated Waitstaff Mobile Application
    A. RightMenus generates a smart AI driven menu and assigns it a QR Code.
    B. RightMenus links the smart AI driven menu to the Portal and to the Waitstaff Mobile Application (c)
    C. RightMenus links the smart AI driven menu to Diners Mobile Application
    D. RightMenus creates the orders placed by diners
    E. RightMenus submits the orders to the Portal
    F. RightMenus submits the orders to the to the Waitstaff Mobile Application
    G. Waitstaff Mobile Application communicates with the Portal.

Website, Portals, Mobile Applications and QR Code or barcode are all interconnected to communicate in cloud through Hosting Servers. Restaurants and their guests sign up on the website. Upon signing up each restaurant guest gets a user account with required detailed dining credentials, on the other hand each restaurant is assigned a dedicated administrative portal (to build and manage content) and a dedicated mobile App (for the waitstaff to manage tables and orders). The content of the restaurant's administrative portal is then QR-Coded or barcoded and a dedicated QR Code or barcode is assigned to the restaurant. The guest must download our mobile App for guests and login to his/her user account with predefined login credentials. Our mobile App for restaurant guests is enabled to decode each assigned QR Code or barcode to give access to the restaurant's content on the restaurant's administrative portal and to all applicable underlying functionalities. QR Codes or Barcodes may be placed on restaurant tables, restaurant items, restaurant entrance door and windows or any other place visible to the restaurant's audience. Restaurant guests must download their mobile App from the App Store or from the iTunes Store. All the components above mentioned are linked to a centralized Administrative Portal where all data and restaurants are managed.

Computer (1) and all peripherals (2) and (3), are connected to Internet; then Website (5) is opened where restaurants and Users signup. Each restaurant is assigned a dedicated Restaurant Portal (6) to create and manage content, assign and manage waiters and tables, a dedicated Mobile Application for waitstaff—Waitstaff App (8) to manage tables and orders and a dedicated QR Code or barcode (11) that Mobile Application for restaurant guests—Guest App (9) scans to access the content on Restaurant Portal (6).

Restaurant guests must download the Mobile Application for restaurant guests—Guest App (9) on their Handset—Mobile phone or Tablets (4) to connect and communicate with Restaurant Portal (6) and Mobile Application for waitstaff—Waitstaff App (8). Website (5), Restaurant Portal (6), Mobile Application for waitstaff—Waitstaff App (8) and Mobile Application for restaurant guests—Guest App (9) are all connector to and communicate with the centralized Administrative Portal (7) through Hosting Servers (10). Restaurant will provide details on all allergens and ingredients of concern in each menu dish or item, User will provide all the list of allergens and ingredients user wants to avoid in the user profile. Restaurant, User and menu credentials are all stored on the Hosting Servers. The backend functionalities are built to track each individual user profile against all listed allergens and ingredients from each menu item. When a match is found, the system automatically triggers a customized alert on the menu if that specific user attempts to select or order an item with allergens of ingredients that are of concern.

How to Make the Invention:

To make this invention, one must craft a software that is able to complete the requisite tasks and provide restaurants and their customers with the platform, portals, Applications and tools here above described.

Practically all elements are necessary. To make the invention work better, it could be crafted to work with Artificial Intelligence and smart devices such as Amazon Alexa, Google Home or the likes to enhance the user experience.

Website and portals can be merged into one single application capable of doing all the tasks described in this invention. Equally, Applications and Portals can also be merged into one website capable of executing the same tasks.

How to Use the Invention:

Restaurants sign up to dedicated portals to create AI-driven menus with enhanced item illustrations (item description, multiple pictures and/or videos, menu in multiple languages), create and manage their reward programs and their virtual gift cards, view and manage their bookings and orders, get analytics and reports made of charts and item performance alerts, and see reviews and suggestions from guests. Waitstaff download the waitstaff App and login to manage guests and orders on assigned tables, take notes and receive payments in App. Restaurant guests sign up and download the App then login to their account to scan QR Codes and barcodes or search for restaurants from a database to make reservations, place orders and make in-app payments, make suggestions, give reviews (for restaurant, waiters, and for each item on the menu). Customers will get allergen alerts when selecting menu item with ingredients of concern where applicable, they can see their order history and their booking history, they can translate a menu into other languages, see their rewards where applicable and save their favorite restaurants for quick access. Restaurants can choose to offer virtual gift cards (rechargeable or not) on this platform where restaurant guests can see and purchase their gift cards, use them or credit them when necessary.

Additionally, this software can be applicable:

IN MEDICAL FIELD: to manage staff, patients and various resources and credentials.

IN EDUCATION: to manage faculty and students credentials and share knowledge.

IN RETAIL & HOSPITALITY: to manage brands, their services and their customers.

What is claimed is:

1. A food allergy management system comprising:
    a first user computer in networked communication with a server;
    wherein the first user computer is programmed comprising a list of user allergies stored in a memory as a data file;
    wherein the server comprises a menu, and a list of ingredients for each menu item, the list comprising known allergens, the menu and the list of ingredients stored in a memory of the server as one or more data files;
    wherein the first user computer is operable to access the menu and the list of ingredients through the networked connection with the server, and is operable to automatically generate customized alerts if at least one of the list of ingredients matches one of the list of user allergies, and further operable to present an alert on a display of the first user computer;
    wherein the automatic generation of customized alerts does not require the manual selection of known allergens; and
    wherein the alert is a pop up window presented over a user interface of the food allergy management system.

2. The system of claim 1 wherein the alert is an icon presented in-line of a user interface of the food allergy management system adjacent to a display of a menu item.

3. The system of claim 1 further comprising a second user computer, wherein the second user computer is operable to display a performance alert for a menu item.

4. The system of claim 3 wherein the first user computer and the second user computer are operable to display a reference number for an order.

5. The system of claim 1 wherein the first computer is further operable to translate a menu item into a plurality of languages.

6. The system of claim 1 wherein the first computer is further operable to display a video of how a menu item is made.

* * * * *